(12) United States Patent
Marquis et al.

(10) Patent No.: US 6,245,070 B1
(45) Date of Patent: Jun. 12, 2001

(54) FORCEPS TISSUE REMOVAL DEVICE

(76) Inventors: James A. Marquis, 13 Pocono Point Rd., Danbury, CT (US) 06811; Germaine M. McCarroll, 631/2 Grassy Plain St., Bethel, CT (US) 06801

( * ) Notice: Subject to any disclaimer, the term of this patent is extended or adjusted under 35 U.S.C. 154(b) by 0 days.

(21) Appl. No.: 09/436,041

(22) Filed: Nov. 8, 1999

(51) Int. Cl.[7] .................................................. A61B 18/14
(52) U.S. Cl. ................................................ 606/51; 606/52
(58) Field of Search ........................................ 606/51, 52

(56) References Cited

U.S. PATENT DOCUMENTS

| | | |
|---|---|---|
| 3,685,518 | 8/1972 | Beuerle et al. . |
| 4,005,714 | 2/1977 | Hiltebrandt . |
| 4,307,720 | 12/1981 | Weber, Jr. . |
| 4,492,231 | 1/1985 | Auth . |
| 4,819,633 | 4/1989 | Bauer et al. . |
| 5,085,657 | 2/1992 | Ben-Simhon . |
| 5,423,814 | 6/1995 | Zhu et al. . |

OTHER PUBLICATIONS

Richard Wolf instruction leaflet E12C–01–94 *Bipolar Instrument Instructions*, Richard Wolf Medical Instruments Corp., 353 Corporate Woods Parkway, Vernon Hills, IL 60661.

*Primary Examiner*—Lee Cohen
(74) *Attorney, Agent, or Firm*—William C. Crutcher

(57) ABSTRACT

A tissue removal device is used with a standard Kleppinger bipolar forceps. A cleaning element held on a tube fitting over the Kleppinger forceps tubes, is used to remove coagulated tissue from between the forceps blades and clean the blades. A motion restrictor also is disclosed which prevents excessive movement of the tissue removal device.

13 Claims, 5 Drawing Sheets

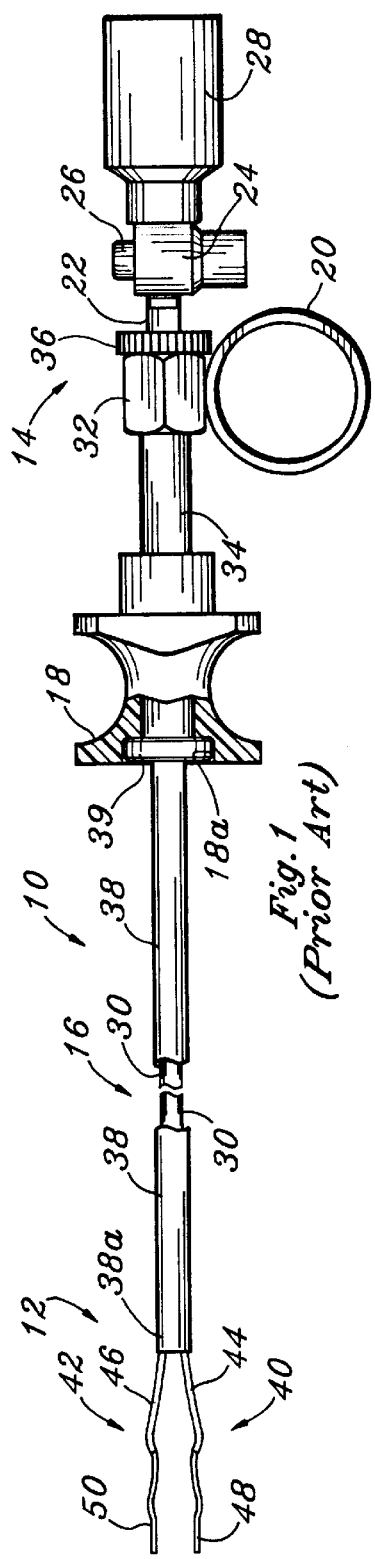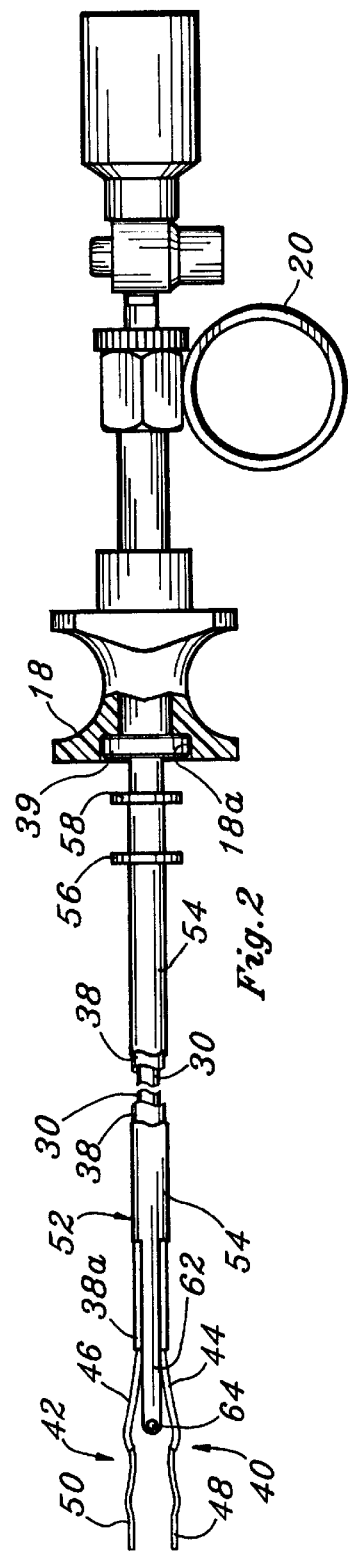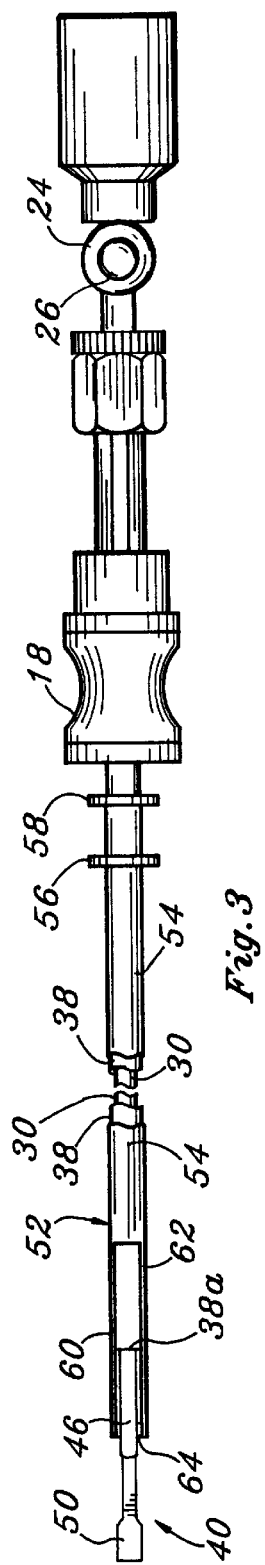

Figure 12:
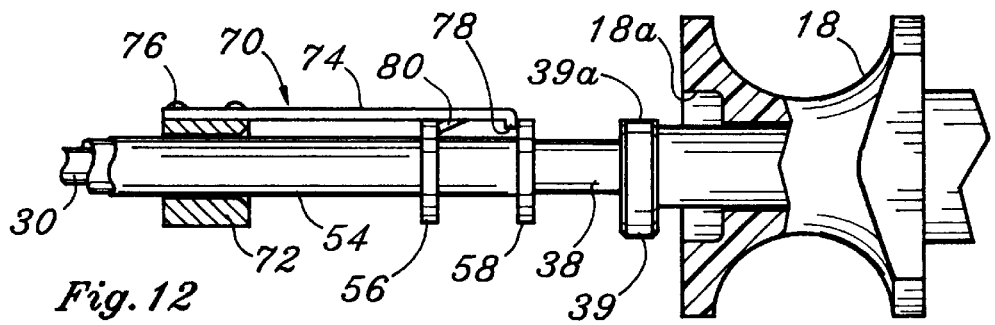

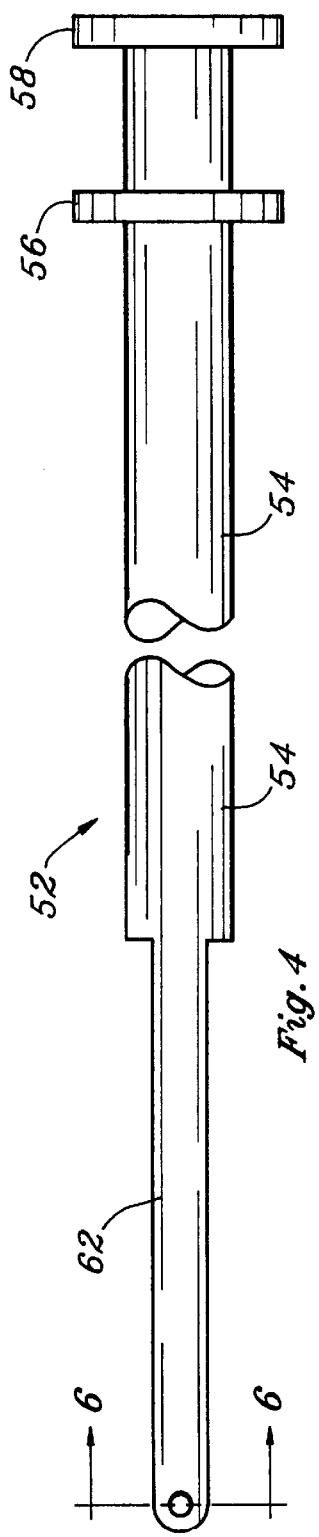
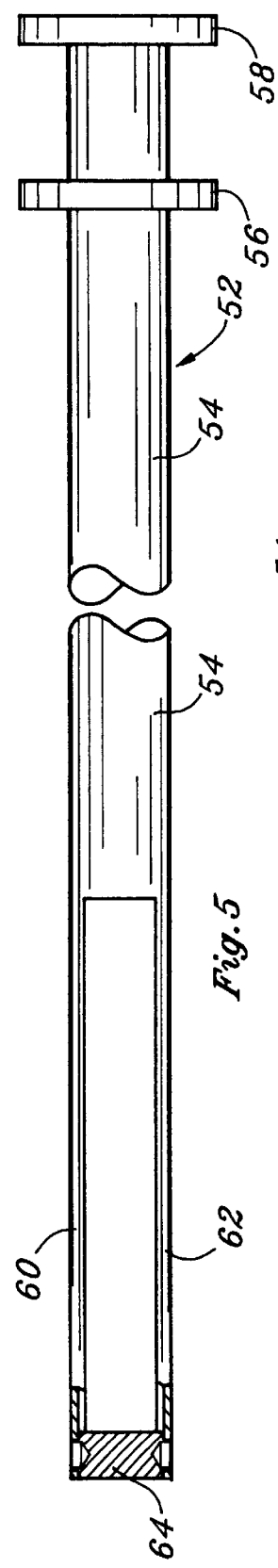
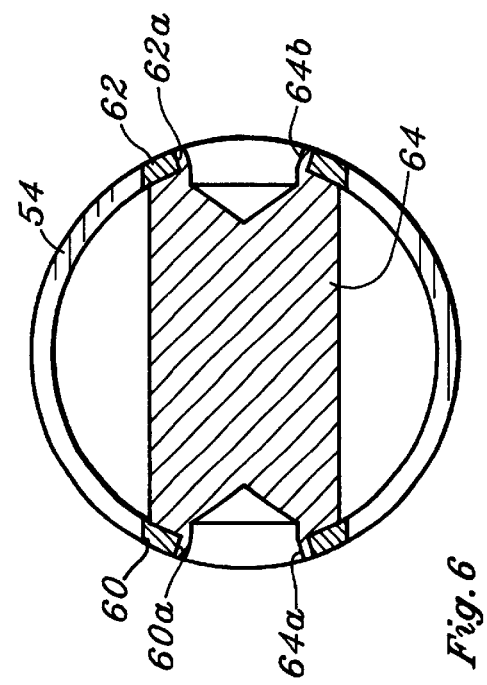
Fig. 4
Fig. 5
Fig. 6

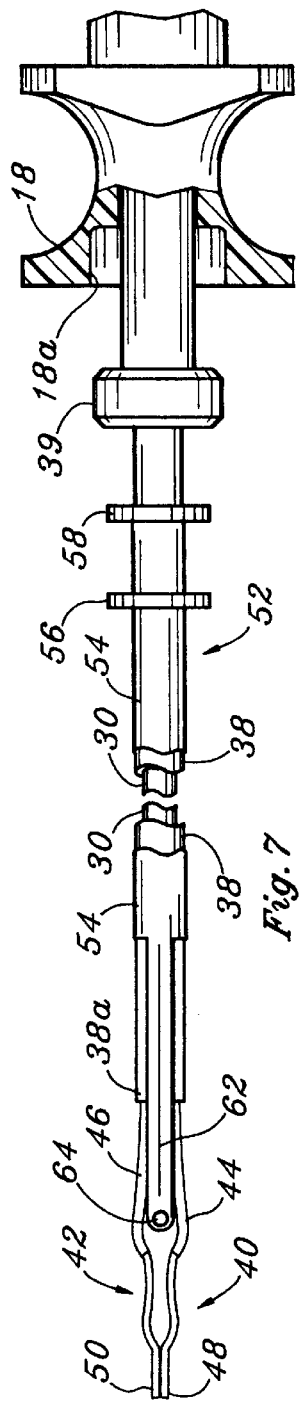
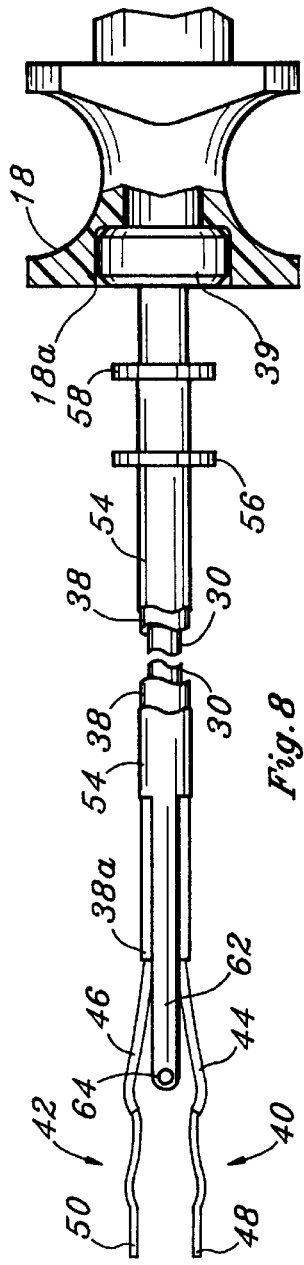
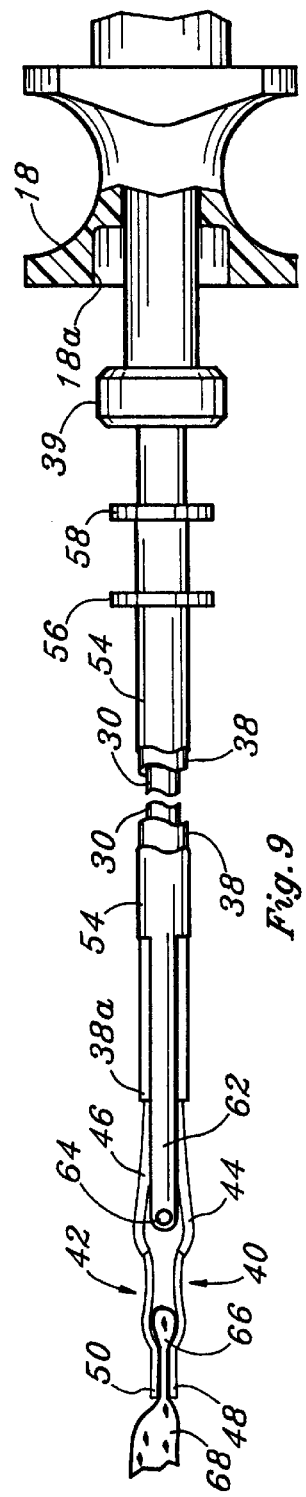

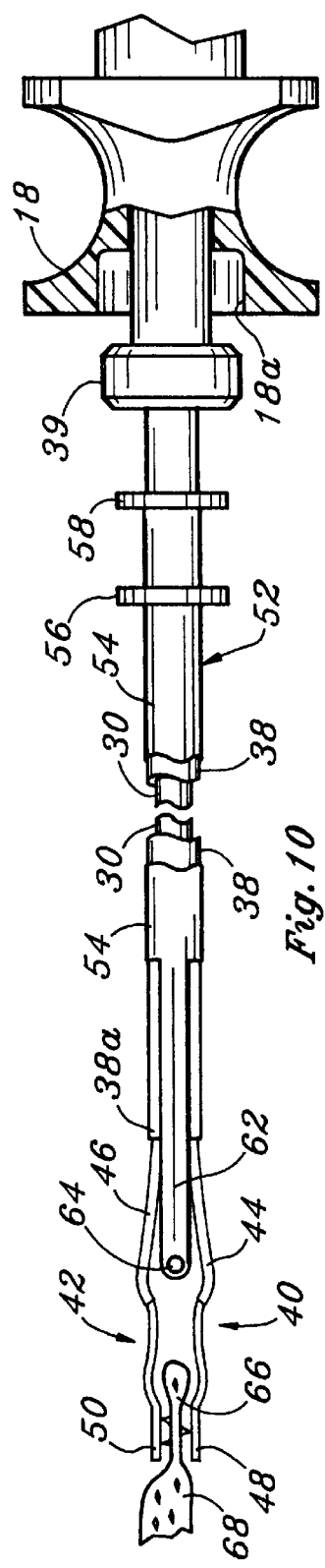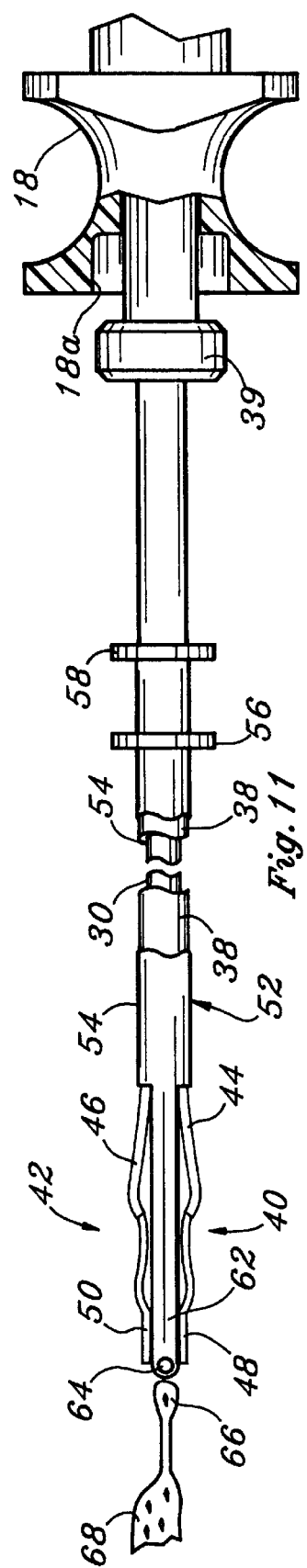

FORCEPS TISSUE REMOVAL DEVICE

This invention relates generally to surgical forceps, especially electrosurgical forceps for coagulating tissue, and more particularly to a tissue removal device for such forceps. The invention is especially useful when employed with bipolar forceps used in endoscopic surgery for cleaning the bipolar electrodes during or following a procedure without removal of the forceps from the patient.

BACKGROUND OF THE INVENTION

Surgical coagulation forceps are well known for performing endoscopic surgery, which involves coagulating tissue held between forceps blades. Coagulation forceps are known both of the monopolar type and the bipolar type, which use intermittent high frequency current. Kleppinger bipolar forceps, which are used in conjunction with Richard Wolf electrosurgical units, provide coagulation by the bipolar method during a well-known procedure for simultaneous coagulation of both the fallopian tube and the mesosalpinx. Kleppinger bipolar forceps are designed with flat, duck-billed tips or blades on the ends of a pair of forceps spring members. The spring members are insulated and contained within a tube, which, when moved axially, forces the forceps blades together. The Kleppinger bipolar forceps may either be of the syringe type or the scissors type, which refers to the type of manual manipulating handle used by the surgeon outside the patient's body.

Illustrative of the prior art are U.S. Pat. No. 4,005,714 issued Feb. 1, 1977 to Hiltebrandt showing a scissors-type bipolar coagulation forceps, and U.S. Pat. No. 4,819,633 issued Apr. 11, 1989 to Bauer et al. showing a monopolar coagulation forceps, both patents being assigned to Richard Wolf GmbH, these patents being incorporated herein by reference. A description of the operation and maintenance of Kleppinger bipolar forceps used with Richard Wolf Bipolar Systems for procedures involving coagulation of the fallopian tube is found in "Bipolar Instrument Instructions" no. E12C-01-94 issued by Richard Wolf Medical Instruments Corp., which is also incorporated herein by reference.

A well known problem with coagulation forceps after coagulation has been performed by high frequency current or other heat generated during surgical procedures is that tissue adheres to the forceps blades that are in contact with the tissue. When the blades are opened and a portion of tissue adheres to the forceps blades, withdrawal of the forceps from the coagulated tissue can tear the tissue and cause bleeding. Another problem is that the residue of tissue adhering to the forceps blades in the form of ash increases the electrical resistance to the flow of current, requiring a longer time to coagulate the tissue than would be possible if the blades were clean. While it is possible to remove the forceps from the patient, disassemble the forceps and clean the forceps blades, this increases the time required by the surgical procedure.

The prior art has addressed the problem of tissue removal from electrosurgical instruments in various ways.

U.S. Pat. No. 5,423,814 issued Jun. 13, 1995 to Zhu et al. describes an endoscopic bipolar coagulation device enabling the user to clean the electrodes during the procedure without removal from the body. The forceps blades are opened and closed by manipulating a tube with respect to a pair of split frustoconical members formed adjacent the tips of the blades. A cleaning element is suspended from a cleaning rod extending inside the tube. The cleaning rod is slid to scrape the inside edges of the forceps blades. A variation uses a tilting mechanism with control wires on pulleys to actuate the cleaning rod. This leads to a congested area inside the tube.

Other techniques for tissue removal are shown by the following patents. U.S. Pat. No. 4,492,231 issued Jan. 8, 1985 to Auth seeks to avoid sticking of tissue by controlling the RF signal. U.S. Pat. No. 3,685,518 issued Aug. 22, 1972 to Beuerle et al. seeks to prevent adherence by making the blades of a thermally and electrically highly conductive material. Lastly, U.S. Pat. No. 4,307,720 issued Dec. 29, 1981 to Weber, Jr. and U.S. Pat. No. 5,085,657 issued Feb. 4, 1992 to Ben-Simhon employ electrosurgical blades which retract into cleaning housings, which scrape adhered tissue from the blades.

With any type of cleaning element or tissue removal element which is moveable with respect to the forceps blades, there is always the danger of over-extension of the cleaning element past the forceps blades, which could cause possible injury. Means to limit the excursions of the cleaning element are also very desirable in a tissue removal device for forceps.

Accordingly, one object of the present invention is to provide an improved tissue removal device for surgical coagulation forceps.

Another object of the invention is to provide an improved tissue removal device for a standard Kleppinger bipolar forceps, which does not require any modification of the Kleppinger forceps, or at most, only minor modification.

Still another object of the invention is to provide an improved tissue removal device for a bipolar forceps with a motion restrictor, which limits excursions of the cleaning device with respect to the forceps blades.

SUMMARY OF THE INVENTION

Briefly stated, the invention comprises a tissue removal device for using with a forceps of a known type having a first tube member including a pair of outwardly biased forceps spring members extending from a distal end thereof, the forceps spring members respectively terminating in forceps blades adapted to grip tissue therebetween, a second tube member coaxially disposed outside of the first tube member and having a distal end adapted to cooperate with the forceps spring members, and forceps manipulating means connected so as to enable an operator to move the first tube member axially with respect to the second tube member, so as to open and close the forceps blades or to hold them spaced apart at an intermediate position, the improved tissue removal device comprising a third tube member coaxially disposed outside of the second tube member and having a pair of spaced arms extending from a distal end thereof, the arms having distal ends and being laterally spaced apart from one another sufficient to allow the forceps spring members to move therebetween, a cleaning element extending between the distal ends of the pair of spaced arms and dimensioned so as to pass between the forceps blades when they are held spaced apart at the intermediate position by the forceps manipulating means, and means for moving the third tube axially with respect to the first tube member to cause the cleaning element to pass between the forceps blades and remove tissue adhering to the forceps blades.

Optionally, the tissue removal device includes motion restrictor means for limiting axial movement of the third tube member with respect to the second tube member by a preselected amount, which is adaptable for use with a standard Kleppinger bipolar forceps without substantial modification.

DRAWINGS

Figure 13:
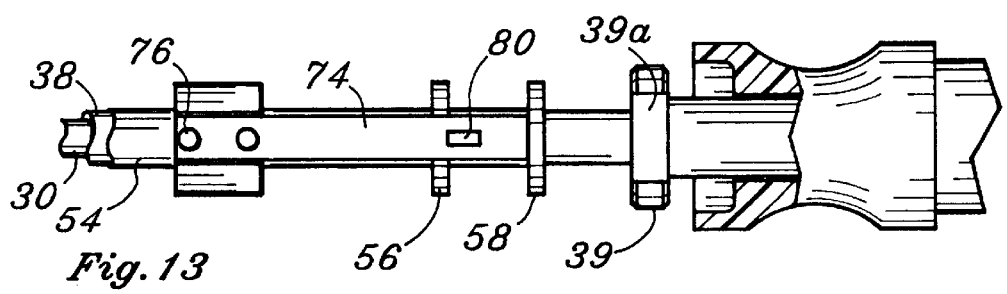
Figure 14:
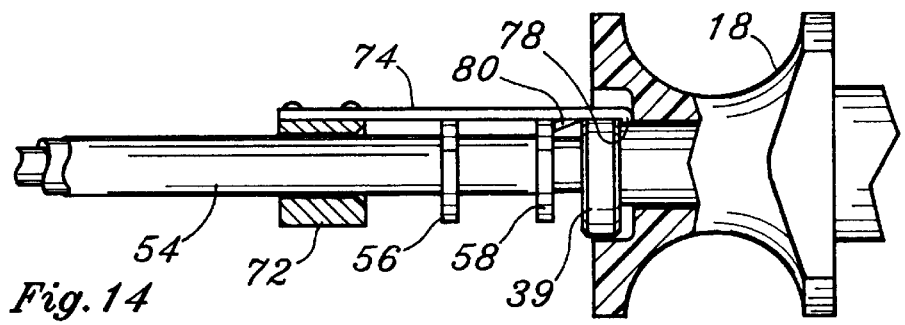
Figure 15:
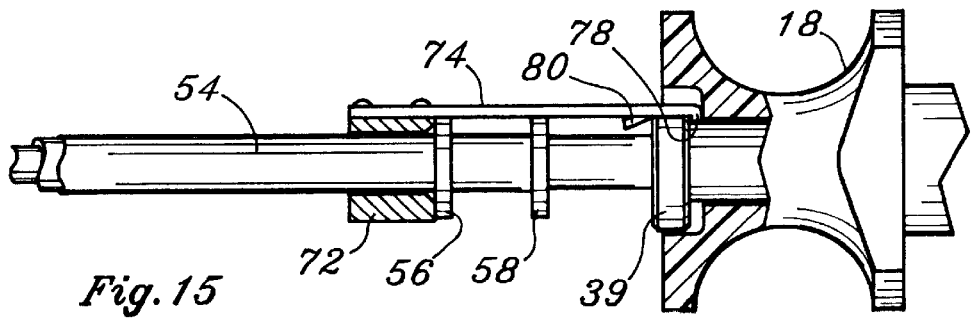

The invention both as to organization and method of practice, together with further objects and advantages thereof, will best be understood by reference to the following description, taken in connection with the accompanying drawings, in which:

FIG. 1 is a side elevational view of the proximal and distal ends of a standard Kleppinger bipolar forceps, with portions of the central section removed in order to shorten the length of the figure on the drawing, FIG. 2 is the same side elevational view of the proximal and distal ends of the bipolar forceps of FIG. 1, but including a tissue removal device according to the present invention, FIG. 3 is a top plan view of the bipolar forceps with tissue removal device shown in FIG. 2, FIG. 4 is an enlarged side elevational view of the proximal and distal ends of the tissue removal device alone, FIG. 5 is a top plan view of the proximal and distal ends of the tissue removal device shown in FIG. 4, FIG. 6 is a further enlarged cross sectional view of the cleaning element, taken along lines 6—6 of FIG. 4, FIGS. 7–11 are side elevational views of the distal and proximal ends of the tissue removal device, along with portions of the bipolar forceps, illustrating the successive relative positions of the elements during operation, FIG. 12 is a side elevational view of a motion restrictor used in conjunction with the tissue removal device shown in one operative position, FIG. 13 is a top plan view of the motion restrictor shown in FIG. 12, FIG. 14 is a side elevational view of the motion restrictor shown in a second operative position with respect to the bipolar forceps, and FIG. 15 is a similar side elevational view showing operation of the motion restrictor in a third operative position.

DESCRIPTION OF THE PREFERRED EMBODIMENT

Referring now to FIG. 1 of the drawing, a prior art Kleppinger bipolar forceps shown generally at 10, includes a distal end 12 which is inserted into the patient's body for endoscopic surgery, and a proximal end 14, which is manipulated by the surgeon outside the patient's body. The distance between distal and proximal ends is much greater than shown on the drawing, consisting of an uninterrupted length of identical construction (not shown) indicated at 16. The overall forceps length is approximately twice the length of the elements shown in the drawing.

On the proximal end 14, a finger guide 18 and a thumb ring 20 are used to manipulate the forceps. Finger guide 18 is connected by a retaining tube 22 to an assembly comprising a shaft coupling 24 with spring loaded release pin 26, and a high frequency electrical power supply socket 28. The latter is adapted to receive a connecting cable (not shown) which connects the forceps with a controlled source of low voltage, high frequency (RF) current, such as a Richard Wolf Electrosurgical Unit.

Extending the length of the forceps is a first tube member 30 the proximal end of which is captured within coupling 24. Thus, finger guide 18 is connected via elements 22, 24 to the first tube member 30, so that they move as a unit.

Thumb ring 20 is welded to a nut 32, which is retained on a shaft member 34 by a threaded nut 36. Shaft 34 forms an extension of a second tube member 38 coaxially disposed outside of the first tube member 30. Thumb ring 20 and finger guide 18 therefor enable an operator to move the first tube member 30 axially with respect to the second tube member 38. The second tube member 38 and shaft member 34 are joined by a flange 39. Finger guide 18 includes a recess 18a, which receives flange 39 and limits movement between first and second tube members.

Extending throughout the length of the first tube member 30 are a pair of insulated conductors (not shown), terminating in a pair of outwardly biased forceps spring members 40, 42. The forceps spring members are insulated over a portion of their length as shown at 44, 46 and terminate in shaped, uninsulated forceps blades designated 48, 50. The uninsulated blades 48, 50 are curved to receive the fallopian tube and terminate in flat duck-billed tips for gripping the mesosalpinx (see FIG. 9). The distal end of the second tube member, designated by reference numeral 38a restrains the forceps spring members and serves to open and close the forceps blades 40b, 42b in a manner well known in the art.

In accordance with the present invention, as illustrated in FIGS. 2 and 3, a tissue removal device, shown generally at 52 comprises a third tube member 54 coaxially disposed outside of the second tube member 38. On the proximal end of third tube member 54 is a pair of spaced flanges 56, 58, which serve as an operating handle used by the surgeon to manually move the third tube member axially. On the distal end of third tube member 54 is a pair of spaced arms 60, 62, best seen in FIG. 3. A cleaning element 64 extends between the distal ends of the pair of spaced arms 60, 62. As best seen in FIG. 3, arms 60, 62 are laterally spaced apart from one another sufficiently to allow the forceps spring members 40, 42 to expand and contract between them. Additionally arms 60 and 62 are shaped by bending them slightly inwardly toward one another in the vicinity of the lead line of reference number 60 in FIG. 3. The shaped arms 60, 62 prevent inadvertent unrestrained movement of tube member 52 relative to tube member 38. Other methods of shaping the surfaces to provide frictional engagement include indented ribs in the third tube member or slight flattening of the third tube member.

Referring to the enlarged views of FIGS. 4, 5 and 6, details of the tissue removal device will be seen more clearly. Spaced arms 60, 62 are most conveniently provided by notching, and removing diametrically disposed, longitudinal sections of the third tube member 54, so that two arms 60, 62 of arcuate cross section remain. Diametrically disposed holes 60a, 62a are drilled in the ends of the respective arms. Cleaning element 64 comprises a cylindrical pin, which is counterbored on opposite ends to leave upstanding circular flanges 64a, 64b. These are expanded or swaged to lock the cleaning element 64 in place between the arms as shown in FIG. 6. The components of the tissue removal device 52 are preferably made of stainless steel and ground smooth on the outer surface. The inner bore of third tube member 54 is dimensioned to fit with reasonably close tolerance over the second tube member outer diameter and to slide freely.

Operation

The operation of this aspect of the invention will be made more clear by reference to FIGS. 7–11 showing successive steps during coagulation of the fallopian tubes and mesosalpinx. FIG. 7 illustrates the forceps blades 48, 50 tightly closed by squeezing the thumb ring (not shown) toward finger guide 18, causing the first tube member 30 to move axially with respect to second tube member 38. This causes the distal end 38a of the second tube member to squeeze the forceps spring members together. The tissue removal device 52 is located such that the cleaning element 64 lies between the insulated portions 44, 46 of the forceps spring members.

Once the coagulation forceps has been introduced into the abdominal cavity through a trocar guide (not shown) the forceps are reopened by retracting the second tube member 38, allowing the forceps spring members 40, 42 to expand. Flange 39 retracts into finger guide recess 18a to limit further expansion. This is shown in FIG. 8.

Now the forceps blades are directed under observation of the surgeon, so that the salpinx or fallopian tube indicated at reference numeral 66 lies within the curved portion of the uninsulated curved portions of forceps blades 48, 50, while the straight duck-billed tips of forceps blades 48, 50 clamp opposite sides of the adjacent mesosalpinx, indicated by reference numeral 68. This is shown in FIG. 9. Coagulation proceeds in a conventional manner by applying high frequency pulses along the conductors within first tube member 30.

After a certain cooling period, the forceps are opened to an intermediate position as shown in FIG. 10 by squeezing the thumb ring toward the finger guide 18. Portions of the salpinx and/or mesosalpinx tissue may adhere to the forceps blades 48, 50 as indicated.

In accordance with the present invention, the tissue removal device 54 is then moved axially with respect to the first tube member, using the flanges 56, 58 to move the third tube member in the direction of the forceps blades. During this cleaning and tissue removal procedure, the forceps blades are held in the intermediate position, where they are closed slightly. The cleaning element 64 will wipe the flat tip portions of the forceps blades while pushing the coagulated portion from between the blades, and freeing any adhered tissue. This step is illustrated in FIG. 11.

By means of the tissue removal device, the coagulated members are gently removed without creating tearing of the tissue. At the same time, the blades are cleaned without the need to remove the instrument from the patient.

Motion Restrictor (Optional)

As apparent from FIG. 11, the surgeon must take care during the tissue removal process, so as not to overextend the third tube member. A motion restricting device is illustrated in FIGS. 12–15, which requires little or no modification of a standard Kleppinger bipolar forceps, and which automatically reduces the likelihood of over-extension of the tissue removal device.

Referring to the side elevation view of FIG. 12 and the top plan view of FIG. 13, the same reference numerals are used with respect to the proximal end of the tissue removal device as in previous figures. The third tube member with spaced flanges 56, 58 is coaxially disposed over the second tube member 38, as before, which in turn is coaxially disposed over first tube member 30. Flange 39 on the second tube member is modified to provide a flat 39a.

A motion restrictor, shown generally at 70 comprises a sleeve 72 arranged to slide on the third tube member 54, and having a flexible spring strip member 74 attached thereto by rivets 76. Spring member 74 has a turned down end tab 78, and a second inside inclined tab 80, these being spaced to fit between flanges 56, 58 as shown in FIG. 12. In this first operative position, the motion restrictor 70 is held on the end of the tissue removal device 52, so they can be handled as a unit.

The operation of the motion restrictor is illustrated in FIGS. 14 and 15. Prior to the tissue removal procedure described in connection with FIG. 11, spring arm 74 is lifted and the end tab 78 slid across flat 39a to hook on the flange 39 of the second tube member. Now the right hand excursion of the third tube member 54 is limited by flange 58 striking the depending tab 80. This is the second operative position, which is shown in FIG. 14.

The left hand excursion of the third tube member 54 is limited by flange 56 striking the sleeve 72. This is the third operative position shown in FIG. 15. This effectively prevents over-extension of the third tube member and limits the axial movement of the third tube member with respect to the second tube member by a preselected amount.

Thus there has been described an improved tissue removal device with means for limiting excessive movement of the cleaning element beyond the forceps blades. The invention has been illustrated in connection with a Kleppinger bipolar forceps, but is applicable to any sort of similar forceps having blades to be cleaned.

What is claimed is:

1. A tissue removal device for using with a forceps of a known type having a first tube member including a pair of outwardly biased forceps spring members extending from a distal end thereof, said forceps spring members respectively terminating in forceps blades adapted to grip tissue therebetween, a second tube member coaxially disposed outside of the first tube member and having a distal end adapted to cooperate with said forceps spring members, and forceps manipulating means connected so as to enable an operator to move the first tube member axially with respect to the second tube member, so as to open and close the forceps blades or to hold them spaced apart at a selectable spaced position, the improved tissue removal device comprising:

a third tube member coaxially disposed outside of the second tube member and having a pair of spaced arms extending from a distal end thereof, said arms having distal ends and being laterally spaced apart from one another sufficient to allow the forceps spring members to move therebetween, a cleaning element extending between the distal ends of the pair of spaced arms and dimensioned so as to pass between the forceps blades when they are held spaced apart at said selectable spaced position by the forceps manipulating means, and means for moving the third tube member axially with respect to the first tube member to cause the cleaning element to pass between the forceps blades and remove tissue adhering to the forceps blades.

2. The combination according to claim 1 and further including means for controlling the axial movement of the third tube member with respect to the second tube member.

3. The combination according to claim 2, wherein said controlling means comprises a motion limiting device for limiting the axial movement of the third tube member with respect to the second tube member by a preselected amount.

4. The combination according to claim 2, wherein said controlling means comprises shaped surfaces on at least one of said tube members causing frictional engagement between the second and third tube members to prevent inadvertent unrestrained movement therebetween.

5. The combination according to claim 4, wherein the shaped surfaces comprise inwardly bent portions of said spaced arms.

6. A tissue removal device for using with bipolar forceps of a known type having a first tube member including a pair of outwardly biased electrically conductive forceps spring members extending from a distal end thereof, said forceps spring members respectively terminating in forceps blades adapted to grip tissue therebetween and arranged to coagulate the tissue gripped between the forceps blades, said forceps spring members having first portions covered with insulating material and extending inside the first tube member and beyond the distal end thereof, and having second uninsulated portions terminating in the forceps blades, a second tube member coaxially disposed outside of the first tube member and having a distal end adapted to cooperate with said forceps spring members, and forceps manipulating means connected so as to enable an operator to move the first tube member axially with respect to the second tube member, so as to open and close the forceps blades or to hold them spaced apart at a selectable spaced position, the improvement comprising:

- a third tube member coaxially disposed outside of the second tube member and having a pair of spaced arms extending from a distal end thereof, said arms having distal ends and being laterally spaced apart from one another sufficient to allow the forceps spring members to move therebetween,
- a cleaning element extending between the distal ends of the pair of spaced arms and dimensioned so as to pass between the forceps blades when they are held spaced apart at said selectable spaced position by the forceps manipulating means, and
- means for moving the third tube member axially with respect to the first tube member to cause the cleaning element to pass between the forceps blades and remove tissue adhering to the forceps blades.

7. The combination according to claim 6 and means for holding the third tube member such that the cleaning element is disposed between the insulated first portions while tissue held between the second portions is being coagulated.

8. The combination according to claim 6, wherein said spaced arms comprise extensions of said third tube member formed by removing diametrically opposite longitudinal portions from the third tube member.

9. The combination according to claim 6, wherein the cleaning element comprises a cylindrical pin having deformable end portions adapted to be deformed to attach the pin between said spaced arms.

10. The combination according to claim 6 and further including means for controlling the axial movement of the third tube member with respect to the second tube member.

11. The combination according to claim 10, wherein said controlling means comprises a motion limiting device for limiting the axial movement of the third tube member with respect to the second tube member by a preselected amount.

12. The combination according to claim 10, wherein said controlling means comprises shaped surfaces on at least one of said tube members causing frictional engagement between the second and third tube members to prevent inadvertent unrestrained movement therebetween.

13. The combination according to claim 12, wherein the shaped surfaces comprise inwardly bent portions of said spaced arms.

* * * * *